United States Patent [19]
Woolf et al.

[11] Patent Number: 5,445,844
[45] Date of Patent: Aug. 29, 1995

[54] FORMULATED FOOD CONTAINING A FREEZE CONCENTRATED LIQUID DAIRY PRODUCT

[75] Inventors: Herbert D. Woolf, Apalchin, N.Y.; Kamendu C. Vasavada, Palatine, Ill.

[73] Assignee: Electric Power Research Institute, Palo Alto, Calif.

[21] Appl. No.: 108,223

[22] Filed: Aug. 19, 1993

[51] Int. Cl.⁶ .............................................. A23C 1/08
[52] U.S. Cl. .................... 426/580; 426/384; 426/385; 426/581; 426/582; 426/583; 426/584; 426/587; 426/588
[58] Field of Search ............... 426/580, 581, 582, 583, 426/584, 587, 588, 384, 385

[56] References Cited

U.S. PATENT DOCUMENTS

| | | | |
|---|---|---|---|
| 4,769,255 | 9/1988 | Ahmed et al. | 426/580 |
| 4,959,234 | 9/1990 | Ahmed et al. | 426/580 |

*Primary Examiner*—Helen Pratt
*Attorney, Agent, or Firm*—Griffin, Butler, Whisenhunt & Kurtossy

[57] ABSTRACT

In a formulated food containing a dairy product and having a significant dairy flavor, improvements are provided when the dairy product is at least in part one physical form of freeze concentrated liquid dairy product in sufficient amount so as to improve at least the dairy flavor of the formulated food.

14 Claims, No Drawings

FORMULATED FOOD CONTAINING A FREEZE CONCENTRATED LIQUID DAIRY PRODUCT

The present invention relates to formulated foods, especially commercially formulated foods, which contain a liquid dairy product, and which may be in a concentrated form, and more particularly to certain such formulated foods which contain at least a dairy flavor and are formulated for use by the consuming public.

BACKGROUND OF THE INVENTION

A wide variety of commercially formulated foods for consumer consumption are prepared with a liquid dairy product, and very often where the liquid dairy product is in a concentrated form, e.g. ice cream, sour cream, white sauces, milk chocolate, salad dressings, and the like. In such commercially formulated foods, a concentrated dairy product is often used, since, otherwise, the excess water of, for example, skim milk or whole milk, must be removed from the formulation during processing into the finished product. This is because the total solids content of the dairy product ingredient or the finished formulated food must be relatively high, and to reach those higher total solids contents, at least some of the water of a natural state liquid dairy product must be removed.

Generally speaking, processes for increasing the solids contents of dairy products can be broadly classified into two categories, i.e. thermal processes and mass transfer processes. Thermal processes involve heating the liquid dairy product to a temperature where the non-solids of the dairy product are evaporated or distilled. Such processes can alter the solids content of the dairy product such that either a relatively highly concentrated dairy product or a dried dairy product is obtained. Typical thermal processes include heat evaporation, oven drying and spray drying.

Mass transfer concentration processes do not normally include a thermal process, or, at least, include a thermal process with substantially less thermal separation than typical thermal processes. Among known mass transfer processes are ultrafiltration, centrifugal separation and freeze drying.

One of the most common forms of concentrated dairy product is that of evaporated milk, either whole milk or reduced fat milk or skim milk. The process involves heating under vacuum and is, in part, therefore, a thermal process. Another common form of concentrated dairy product is the powdered form, achieved by spray drying, which, again, is a thermal process. Mass transfer processes are far less commonly used than thermal processes, since the thermal processes are easier to operate and considerably less inexpensive. However, one mass transfer process, i.e. ultrafiltration, has found applicability for concentrating liquid dairy products where it is desired, during the concentrating step, to remove other components of the liquid dairy product, e.g. ash and the like, in addition to water removal.

Accordingly, as a general statement, most of the concentrated dairy products are made by thermal processes, including vacuum pan evaporation, heat evaporation and spray drying. However, as is well known, these thermal processes, unfortunately, alter the taste, texture and mouth feel of the resulting concentrated product. For example, evaporated skim milk or whole milk has a taste, texture and mouth feel, either in the concentrated form or in the reconstituted form (reconstituted with water), which is substantially different from the taste, texture and mouth feel of the fresh milk. In addition, the functionality of the evaporated milk, as opposed to fresh milk, is changed during that thermal processing. For example, evaporated milk cannot be used in certain types of cooking and baking, as opposed to fresh milk, and evaporated whole milk, while having a fat content similar to cream, cannot be effectively whipped into a traditional whipped cream. On the other hand, as is also well known, spray dried skim milk or whole milk, when reconstituted with water, has a somewhat cooked taste, which is quite objectionable to large numbers of people.

Thus, as a practical matter, in formulated foods containing a concentrated dairy product, the art has, essentially, been restricted to evaporated or spray dried dairy products, i.e. in the concentrated, partially reconstituted or fully reconstituted form, but both of these introduce unwanted tastes, textures and mouth feel to the formulated foods. The general approach in the art in connection with the unwanted taste is to overpower that unwanted taste by the inclusion of relatively large amounts of the flavoring used in the formulated food. For example, in ice cream, evaporated milk and/or spray dried milk powder may be used, but, to mask unwanted flavors, the amount of the flavoring of the ice cream, e.g. vanilla, is considerably increased beyond that which would be necessary if the ice cream had been made from formulations which do not include a concentrated form of the dairy product, but instead include fresh skim or whole milk or cream.

However, the defects introduced into such formulated foods by conventional concentrated dairy products in terms of texture and mouth feel have never been adequately dealt with by the art, and these defects continue in such formulated foods. A notable example thereof is ice cream made with concentrated dairy products, where the undesired flavors thereof are masked by high proportions of flavoring materials, and the undesired texture and mouth feel are masked by use of relatively large amounts of gums and thickeners. While such gums and thickeners do mask the undesired mouth feel of such products, they also introduce other unwanted textures and mouth feels, and, therefore, the use of such gums and thickeners is a definite compromise in the art.

Similar problems exist with other foods formulated with concentrated dairy products, such as cultured foods, e.g. low fat or imitation sour cream or cream cheese, as well as cooked foods, e.g. white sauces and soups. The problem also exists in other formulated food mixtures using concentrated dairy products, e.g. milk chocolate and salad dressings. In these other various foods, the art has taken a number of different approaches to mitigate the undesired flavors, mouth feel and texture, but, here again, all of these approaches result in definite compromises, similar to the ones described above in connection with ice cream.

It would, of course, be of considerable advantage to the art to eliminate these difficulties with formulated foods containing concentrated dairy products, but, as noted above, all prior efforts in the art, using conventionally produced concentrated dairy products, produced less than desired results.

However, in commonly assigned U.S. Pat. No. 4,959 234 a method is disclosed for concentrating liquid dairy products, wherein that concentration is effected by a freeze concentration process. A freeze concentration process should be carefully distinguished from a freeze drying process, which is entirely different and produces a dried solid material, e.g. the process used for making freeze dried soluble coffee. In the patented process, a liquid dairy product is cooled to a temperature at or below its freezing point. Formed ice crystals are recrystallized from the cooled liquid dairy product to produce a mixture of concentrated product and ice crystals. A portion of the ice crystals is separated from the mixture and heated to form a melt. The mixture is washed with the melt to form a washed mixture of the concentrated product and the ice crystals. The ice crystals are separated from the washed mixture, and the concentrated product is recovered. That process is described in detail in that patent and will not be repeated herein, for sake of conciseness, and the entire disclosure of that patent is incorporated herein by reference.

That U.S. Pat. No. 4,959,234 goes on to disclose that the freeze concentrated liquid dairy products of that process have improved taste, texture and mouth feel, as opposed to the conventionally concentrated dairy products, either in the concentrated form or in the reconstituted form thereof, when the freeze concentration process is carried out to the extent that the freeze concentrated liquid dairy product has a solids content of at least 20%, and when the solids contents is at least about 30% or more, a very significant increase in the improvements of taste, texture and mouth feel is achieved. For example, when the freeze concentrated liquid dairy product is derived from skim milk, and the concentrated product is reconstituted with water to produce substantially the same solids content as that of the skim milk originally fed to the process, the taste is much more similar to reduced fat milk, e.g. 2% milk, than to skim milk. Further, the texture is far more creamy than skim milk, e.g., the texture is similar to whole milk. The mouth feel is not the watery mouth feel of skim milk, but has a mouth feel similar to reduced fat milk, e.g. 2% fat milk. In addition, that patent points out that freeze concentrated skim milk is whipable, as opposed to the unwhipable nature of evaporated milk.

Accordingly, that patent describes a new concentrated liquid dairy product, i.e. the described freeze concentrated liquid dairy product, which new product does not suffer from the difficulties described above in connection with taste, texture and mouth feel. It was, therefore, expected that the use of such freeze concentrated liquid dairy products in formulated foods should, at least in part, avoid the difficulties of those formulated foods when using conventionally concentrated dairy products, as described above.

SUMMARY OF THE INVENTION

While, from the disclosure of U.S. Pat. No. 4,959,234, it was expected that the freeze concentrated liquid dairy product would reduce the unwanted off taste, mouth feel and texture of conventionally concentrated dairy products in formulated foods, it has now been discovered that not only are those unwanted properties mitigated or avoided, but, most unexpectedly, the use of freeze concentrated liquid dairy products in certain formulated foods actually considerably improves the organoleptic properties thereof, as opposed to such foods made with the natural form of the dairy products. This effect in regard to certain formulated foods was quite unexpected and surprising, since, ordinarily, it would have been assumed that the freeze concentrated liquid dairy products would function, at best, only as well as the natural form of those products, e.g. freeze concentrated skim milk would produce, hopefully, the same functionality and taste of fresh skim milk in a formulated food. This assumption, however, turned out to be wrong, and the organoleptic properties of certain formulated food, using the present freeze concentrated liquid dairy products, are superior to those properties of the conventionally formulated foods using the natural form of the dairy products.

The reasons for these unexpected improvements in organoleptic properties of these certain formulated foods is not fully understood and, while not being bound by theory, it is believed that during the freeze concentrating process some hydration of the milk proteins occur and some lactose is physically separated therefrom, while at the same time the more delicate dairy flavors are not destroyed or lost, as would occur in a thermal concentrating process. Apparently, this altered functionality of the freeze concentrated liquid dairy product provides a synergistic effect with other ingredients in certain formulated foods, and this synergistic effect produces a further improvement in organoleptic properties. The formulated foods which exhibit this synergistic effect are frozen foods, cultured foods, cooked foods and food mixtures.

Thus, very briefly stated, in formulated foods containing a dairy product and having a significant dairy flavoring, the present invention provides the improvement wherein the dairy product is at least in part one physical form of freeze concentrated liquid dairy product in sufficient amount so as to improve at least the dairy flavor of a formulated food selected from the group consisting of a frozen food, a cultured food, a cooked food and a food mixture.

The organoleptic properties are particularly improved in regard to certain of these formulated foods, and especially in connection with, for example, ice cream and soft serve ice milk, sour cream, cream cheese and yogurt, white sauces, cream-style soups, milk chocolate and dairy-style salad dressing. However, the improved organoleptic properties are also dependent upon the degree of freeze concentration of the freeze concentrated liquid dairy product, and for this reason, the total solids content of the freeze concentrated liquid dairy product should be at least 20% and up to 50%, and more preferably at least 30% or 35% and up to 45%.

DETAILED DESCRIPTION OF PREFERRED EMBODIMENTS

As noted above, the present invention provides an improvement in certain formulated foods containing a dairy product and having a significant dairy flavor, wherein the dairy product is a physical form of freeze concentrated liquid dairy product and, thus, provides improved organoleptic properties, at least improved dairy flavor, to those formulated foods. The freeze concentrated liquid dairy product, per se, is described in detail in the above-noted U.S. Pat. No. 4,959,234 (commonly assigned), and the details of that description will not be presented herein. However, very briefly, the freeze concentrated liquid dairy products of that patent are concentrated such that the solids content is at least 20%, especially at least 30% or 35% and up to 50%, especially up to 45%. This will result in a freeze concentrated liquid dairy product which has a viscosity of at least 100 CST and up to about 2,000 CST. However, the present unexpected and significantly improved organoleptic properties, especially improved taste and especially in connection with the certain formulated foods, are further increased when the total solids content is at least 30% and up to about 45% and the viscosity is at least 150 CST and up to about 1,500 CST. The process of producing the defined freeze concentrated liquid dairy product is that as described above.

Thus, for purposes of the present specification and claims, the term freeze concentrated liquid dairy product is defined as being a liquid dairy product which has undergone freeze concentration by removal of in situ formed frozen ice crystals with a wash of melted ice crystals, as described and identified in the aforenoted U.S. Pat. No. 4,959,234.

The concentrated liquid dairy product may be concentrated from a wide variety of dairy products in their natural state, e.g. skim milk, reduced fat milk (1%, 2% and 3%, etc. ), whole milk, cream, buttermilk, and even reconstituted non-fat milk solids. In this latter regard, such non-fat milk solids will retain the undesired flavors which occur in producing such non-fat milk solids, e.g. spray drying, but the other organoleptic properties, especially texture and mouth feel, will be improved during the freeze concentration process.

The formulated foods may be any of the above-noted conventional commercially formulated foods which contain a dairy product and have a significant dairy flavor. It is in connection with such formulated foods that the present unexpected and substantially improved organoleptic properties and superior results are achieved. In this regard, with the freeze concentrated liquid dairy product of the present invention, substantially less flavoring is required, as opposed to conventional amounts of flavoring in such formulated foods, because the present freeze concentrated liquid dairy product does not have the unwanted taste of conventionally concentrated dairy products. Hence, additional flavoring is not required to mask those unwanted tastes.

In addition, the synergistic effect between the freeze concentrated liquid dairy product, as briefly noted above, and other ingredients in the described formulated foods, produce such clear and organoleptically detectable dairy flavor notes that the dairy flavor of the formulated foods is enhanced, even at low amounts of dairy flavoring, and such flavor enhancement produces very notably improved taste. For example, when an industry standard hard-packed ice milk formulation is prepared with the usual liquid skim milk and spray dried skim milk powder, and that same formulation is prepared with the exception that the present freeze concentrated liquid dairy product is substituted for the liquid skim milk and the present freeze concentrated skim milk powder (as discussed more fully below in connection with the powder) is substituted for the spray dried skim milk powder, the overall flavor increases from a sensory score of 4.7 to 6.1, which is equal to a quite unexpected 30% improvement in overall flavor. This is achieved solely by substitution of freeze concentrated skim milk and skim milk powder for the natural skim milk and conventional spray dried skim milk powder. In addition, with that substitution, the dairy flavor notes increases a most unexpectedly 45% in sensory evaluation, which shows the synergistic effect of the present freeze concentrated material in connection with dairy flavor components.

As briefly noted above, these very surprising and unexpected results, as shown in more detail below, have been found in connection with the above-noted certain formulated foods. Thus, the very unexpected and surprising improvement in organoleptic properties is provided when the formulated food is a frozen food, such as ice cream, ice milk and soft serve ice milk. These improved organoleptic properties are also provided when the food is a cultured food, such as sour cream, cream cheese and yogurt (either in the freshly cultured state or frozen state). Very unexpectedly, these improved organoleptic properties are also maintained to a significant degree when the formulated food is a cooked food, such as a white sauce or cream and/or milk-style soups. This is most surprising in that it would ordinarily be expected that the freeze concentrated product, when being cooked in a cooked formulated food, would suffer the disadvantages of off flavors and tastes, as would milk products that had been concentrated in a thermal process. However, most surprisingly, this turned out not to be the case, and the improved organoleptic properties are still significantly maintained in such cooked foods.

Somewhat similarly, it was most surprisingly found that the improved and unexpected organoleptic properties could also be achieved when the formulated food is a food mixture, especially highly dairy flavored food mixtures, such as milk chocolate and dairy-style salad dressings.

Another most surprising aspect of the present invention is that the freeze concentrated liquid dairy product may be in the physical form of a dried powder, and the improved and synergistic organoleptic properties are largely maintained. This is quite surprising, since it would have been expected that these improved organoleptic properties would have been substantially reduced or even off flavors introduced during drying, in view of the long experience in the art that drying dairy products introduce off flavors, e.g. in spray dried milk products. While the reason for the retention of these improved organoleptic properties during drying is not fully understood, it is believed that hydration of the protein, and possibly some reduction in lactose, as described below, as well as the smaller volume of water which must be removed during drying, allows the drying to take place, especially under mild drying conditions, such that a dried physical form of the freeze concentrated liquid dairy product still retains most of the improved organoleptic properties and synergistic function. The ability to produce such a dried product has very substantial benefits in connection with formulated foods, since industry standard formulated foods often contain dried dairy products. Thus, this is a important feature of the invention, and a quite unexpected one.

As a further feature, especially in regard to the dried physical form of the present freeze concentrated liquid dairy products, it was found that freeze concentration of whole milk was difficult to process, presumably because of the high fat content thereof and the interference of that fat in the crystallization and recrystallization processes during freeze concentration. However, it was found that a whole milk could easily be produced by freeze concentrating skim milk and adding to the freeze concentrated skim milk sufficient cream to bring the mixture to a fat content of whole milk. That whole milk mixture could then easily be dried with a conventional fluidized bed spray drier, under conventional drying conditions, to produce whole milk powder. Likewise, any range of fat contents in the dried powder could be produced simply by adjusting the amount of cream added to the freeze concentrated skim milk.

The present freeze concentrated and dried powder, whether skim milk or any range of fat content added thereto, can be used in industry standard formulations as a substitute for the conventional powdered dairy product component, or it may be reconstituted to original solids content, or any lesser solids content, and used as a liquid component of such formulations. Therefore, in such formulated foods, the freeze concentrated liquid dairy product may be a reconstituted form, e.g. reconstituted to the solids content of the natural product, of the dried freeze concentrated liquid dairy product, and, in addition, the dried form thereof may be used as the dried dairy product component of industry standard formulations. Similarly, the freeze concentrated liquid dairy product of the formulated food may be a reconstituted physical form thereof, e.g. reconstituted to the solids content of the natural product.

As noted in U.S. Pat. No. 4,959,234, during the freeze concentration process, lactose crystals separate and may be removed so as to produce a reduced lactose content freeze concentrated liquid dairy product. While not necessary for most food formulations, conventional formulations with conventional liquid dairy products and conventional dried dairy products will retain essentially all of the original lactose in those dairy products. Many people are lactose intolerant, and, accordingly, those conventionally formulated foods cannot be safely consumed by those persons. However, with the present invention, the freeze concentrated liquid dairy product may have a reduced lactose content, achieved in the manner described in that patent, and formulated foods made with that reduced lactose freeze concentrated liquid dairy product are, therefore, more safe for consumption by these sensitive individuals and, as such, forms a very desirable feature of the present invention.

The dairy flavoring for the formulated food may be essentially as desired, either natural or artificial, as well as dairy flavors developed by the ingredients of the food. For example, the flavors may develop in a food, e.g. during culturing, such as sour cream, cheese, yogurt and buttermilk flavors, and the like. The reason such a wide variety of dairy flavors can be used in the present formulated foods is that the freeze concentrated product (whether in the freeze concentrated liquid physical form, reconstituted physical form or the powdered physical form) not only adds no unwanted off flavors, which must be masked or otherwise hidden, but introduces significantly improved and unexpected organoleptic properties, and synergistic properties, in connection with the above-noted formulated foods.

In view of the foregoing, the amount of the dairy flavor is not critical and may be as desired, so long as that flavor is in a significant amount, i.e. organoleptically detectable. Usually the amount of flavor will be about the same as or less than the amount in the formulated foods having natural or conventionally concentrated dairy products.

The invention will be further understood from the following examples, which are non-limiting examples and simply illustrate the invention, and wherein all percentages and parts are expressed by weight, unless otherwise indicated, as is the case with the foregoing specification and following claims.

EXAMPLE 1

Preparation of Freeze Concentrated Skim Milk and Powdered Form Thereof

The general procedure for producing the freeze concentrated skim milk is essentially that as described in U.S. Pat. No. 4,959,234, and particularly in Example 1 thereof, using the apparatus disclosed in that example, with reference to the specification of that patent.

Fresh skim milk was processed in the manner described in Example 1 of that patent over a processing time of approximately 180 hours of steady state operation to produce 2,660 gallons of freeze concentrate, averaging 37.53% total solids. The maximum concentration level achieved during the run was 39.9%, and the viscosity reached 1400 CST at that highest concentration level. Lactose precipitation was 11.8%. The dewatering rate during the steady state operation averaged 319 liters per hour, with a range of 227 to 480 liters per hour. The lowest solids concentration during the run was about 32%.

A portion of the product was dried in a conventional fluidized bed spray drier, under conventional drying conditions, to a dry free-flowing powder having a moisture content of about 1% or less.

EXAMPLE 2

Preparation of Freeze Concentrated Whole Milk and Powdered Form Thereof

A portion of the liquid product of Example 1 was mixed with cream to produce a mixed whole milk product with a fat content of about 3.8%.

A portion of this mixture was spray dried in a conventional fluidized bed spray drier, under conventional drying conditions, to a whole milk powder having a moisture content of about 1% or less.

In each of the following examples, formulated foods were prepared utilizing industry standard commercial formulations and preparation methods for the foods involved, and the formulated foods were judged by a Panel consisting of five judges who had been screened and trained to evaluate, articulate and quantify flavor and texture attributes of the formulated foods. The evaluations were performed in a light and temperature controlled Panel Room. The formulated foods were presented "blind" to the judges, and were coded with random triple digit numbers. Between attribute evaluation, the judges cleansed their palates with unsalted crackers and water. Attributes were quantified in a sequential monadic study design. All attribute evaluations included color, aroma, flavor and texture, including presence/level of off-flavors, and were specifically chosen to reflect established characteristics of the formulated foods being evaluated. Other appropriate evaluations were also made for each food, for instance, the stability of the salad dressing emulsions, the presence/size of ice crystals in ice milk, and viscosity/texture of the sauce.

With attribute differences $\geq 1.0$, the data were subjected to statistical analysis. Attribute differences $\geq 1.0$, with a $p \leq 0.5$, obtained as a result of a Student t-Test, were required before an attribute of one food was considered significantly different (e.g. superior) from that of another food.

The following formulated foods were prepared using industry standard formulations and prepared by industry standard methods obtained from standard books, ingredient suppliers, or non-proprietary files as controls. In each case, the particular relevant ingredient, such as liquid skim milk, was replaced in the control formulation with liquid freeze concentrate, either reconstituted or not. All of the standard formulations were either unmodified or modified only slightly to make appropriate adjustments.

As will be seen from the following examples, the principle observation resulting from the attribute evaluation data is that formulated foods were judged superior when freeze concentrate ingredients were employed, as compared to the controls.

EXAMPLE 3

Hard Pack Ice Milk (2% Fat)
Standard Formulation Controls

| | Percent | |
|---|---|---|
| Ingredient | Control-1 Skim Milk | Control-2 Skim Milk + WPC |
| Skim milk, liquid | 69.45 | 69.45 |
| Heavy cream (37% fat) | 5.4 | 5.4 |
| Skim milk powder | 6.4 | 3.15 |
| Sugar | 12.0 | 12.0 |
| Corn syrup solids, 36DE | 6.0 | 6.0 |
| Stabilizer gum | 0.45 | 0.45 |
| Vanilla | 0.30 | 0.30 |
| Whey Protein concentrate | — | 3.25 |

Two standard control formulations were used in this test, i.e. with and without whey protein concentrate (WPC). In each control, the skim milk, liquid and skim milk powder were replaced by the same amount of the freeze concentrate and freeze concentrate powder of Example 1, and designated tests 1 and 2. The results are shown below.

| Attributes | Control-1 | Test-1 | Control-2 | Test-2 |
|---|---|---|---|---|
| 1. Color (0 = too light, 4 = about right, 8 = too dark) | 4.0 | 4.0 | 4.0 | 3.8 |
| 2. Aroma* | 2.2 | 2.6 | 2.2 | 2.3 |
| 3. Spoonability (0 = too soft, 4 = about right, 8 = too hard) | 3.5 | 4.6 | 5.0 | 4.1 |
| 4. Overall Flavor* | 4.7 | 6.1 | 6.0 | 6.8 |
| 5. Sweet* | 4.2 | 4.2 | 4.6 | 5.1 |
| 6. Sour* | 0.4 | 0.2 | 0.0 | 0.0 |
| 7. Salty* | 0.0 | 0.0 | 0.0 | 0.0 |
| 8. Bitter* | 0.0 | 0.0 | 0.0 | 0.0 |
| 9. Dairy* | 3.6 | 5.2 | 5.4 | 6.5 |
| 10. Off Flavor* | 0.4 | 0.2 | 0.0 | 0.8 |
| 11. Creaminess* | 3.0 | 5.4 | 3.8 | 5.4 |
| 12. Mouth feel (0 = very gritty 8 = very smooth) | 5.0 | 6.7 | 5.7 | 6.8 |
| 13. Mouth clearing (0 = rapid, thin watery; 4 = about right; 8 = slow, thick, gummy) | 2.8 | 4.1 | 3.2 | 4.6 |
| 14. Iciness* | 2.6 | 0.6 | 2.1 | 0.8 |

0 = none; 8 = extensive

From the above data, it will be seen that the hard pack ice milks (2% fat) prepared with the freeze concentrate products had significantly better overall flavor (p=0.02), dairy notes (p<0.01), mouth feel ("smoother") (p<0.01), and mouth clearing (p<0.01) than the controls. Additionally, the freeze concentrates were perceived to be creamier (p<0.01), less icy (p<0.01), and more spoonable (p=0.01) than the controls.

EXAMPLE 4

Soft Serve Ice Milk (2% Fat)
Standard Formulation Controls

| | Percent | |
|---|---|---|
| Ingredient | Control-1 | Control-2 |
| Skim milk | 72.85 | 72.85 |
| Heavy cream (37% fat) | 5.4 | 5.4 |
| Skim milk powder | 5.0 | 2.0 |
| Sugar | 12.0 | 12.0 |
| Corn syrup solids, 36DE | 4.0 | 4.0 |
| Stabilizer | 0.45 | 0.45 |
| Vanilla | 0.30 | 0.30 |
| Whey Protein concentrate | — | 3.0 |

Two standard control formulations were used in this test, i.e. with and without whey protein concentrate (WPC). In each control, the skim milk and skim milk powder were replaced by the same amount of the freeze concentrate liquid and freeze concentrate powder of Example 1, and designated tests 1 and 2. The results are shown below.

| Attributes | Control-1 | Test-1 | Control-2 | Test-2 |
|---|---|---|---|---|
| 1. Color (0 = too light, 4 = about right, 8 = too dark) | 4.0 | 4.0 | 3.9 | 3.8 |
| 2. Aroma* | 1.2 | 1.6 | 2.1 | 1.4 |
| 3. Spoonability (0 = too soft, 4 = about right, 8 = too hard) | 3.1 | 4.0 | 3.8 | 3.8 |
| 4. Overall Flavor* | 4.2 | 5.9 | 5.7 | 6.5 |
| 5. Sweet* | 3.5 | 3.4 | 4.1 | 3.5 |
| 6. Sour* | 0.0 | 0.0 | 0.0 | 0.0 |
| 7. Salty* | 0.0 | 0.0 | 0.0 | 0.0 |
| 8. Bitter* | 0.0 | 0.0 | 0.0 | 0.0 |
| 9. Dairy* | 4.4 | 5.4 | 5.3 | 6.3 |
| 10. Off Flavor* | 0.0 | 0.0 | 1.5 | 0.5 |
| 11. Creaminess* | 6.2 | 6.7 | 6.7 | 7.5 |
| 12. Mouth feel (0 = very gritty 8 = very smooth) | 6.7 | 7.1 | 6.8 | 6.9 |
| 13. Mouth clearing (0 = rapid, thin watery; 4 = about right; 8 = slow, thick, gummy) | 4.0 | 4.0 | 4.6 | 4.3 |
| 14. Iciness* | 0.0 | 0.0 | 0.0 | 0.0 |

0 = none; 8 = extensive

Test 1 was judged to have superior overall flavor (p<0.01) and dairy flavor (p=0.04) when compared to its control. Test 2 was judged to possess an increased level of overall flavor (p<0.02) and showed a trend toward improved dairy flavor (p<0.06) characteristic of a soft serve ice milk when compared to its control.

EXAMPLE 5

Sour Cream
Standard Formulation Control

| Ingredient | Percent |
|---|---|
| Heavy Cream (37% fat) | 32.50 |
| Skim milk, liquid | 57.47 |
| Skim milk powder | 10.00 |
| Lactic acid culture (DSG 2000 Chr. Hansen's Laboratory) | 0.02 |
| Enzyme (Rennilase XL Novo | 0.01 |

-continued

| Sour Cream Standard Formulation Control | |
|---|---|
| Ingredient | Percent |
| Nordisk) | |

The skim milk, liquid, and skim milk powder of the control were replaced by the same amount of the freeze concentrate liquid and freeze concentrate powder of Example 1 and designated test. The results are shown below in connection with tests done at 36 hours and at 7 days.

| Evaluation at 36 Hours | | |
|---|---|---|
| Attributes | Control | Test |
| 1. Color (0 = too light; 4 = about right; 8 = too dark) | 4.1 | 4.0 |
| 2. Dairy Aroma* | 3.2 | 4.3 |
| 3. Overall Flavor* | 6.0 | 5.7 |
| 4. Sweet* | 1.5 | 1.1 |
| 5. Salty* | 1.5 | 0.8 |
| 6. Sour* | 3.7 | 2.7 |
| 7. Bitter* | 0.2 | 0.0 |
| 8. Dairy* | 3.6 | 4.8 |
| 9. Off Flavor* | 0.2 | 0.0 |
| 10. Creaminess* | 5.7 | 5.5 |
| 11. Mouth coating/ mouth feel (0 = very thin, watery; 4 = about right; 8 = very thick, heavy) | 3.6 | 3.3 |
| 12. Mouth clearing (0 = rapid; 4 = about right; 8 = slow) | 4.0 | 3.3 |
| pH | 4.55 | 4.55 |

*0 = none; 8 = extensive

| Evaluation at 7 Days | | |
|---|---|---|
| Attributes | Control | Test |
| 1. Color (0 = too light; 4 = about right; 8 = too dark) | 4.3 | 4.0 |
| 2. Dairy Aroma* | 3.8 | 3.8 |
| 3. Overall Flavor* | 5.9 | 6.0 |
| 4. Sweet* | 1.1 | 1.0 |
| 5. Salty* | 1.3 | 1.3 |
| 6. Sour* | 3.8 | 4.0 |
| 7. Bitter* | 0.0 | 0.3 |
| 8. Dairy* | 5.0 | 4.5 |
| 9. Off Flavor* | 0.3 | 0.0 |
| 10. Creaminess* | 4.9 | 4.9 |
| 11. Mouth coating/ mouth feel (0 = very thin, watery; 4 = about right; 8 = very thick, heavy) | 4.3 | 3.6 |
| 12. Mouth clearing (0 = rapid; 4 = about right; 8 = slow) | 4.6 | 4.0 |
| pH | 4.5 | 4.5 |

0 = none; 8 = extensive

The sour cream prepared with the freeze concentrate ingredients was judged after 36 hours to have a significantly better dairy aroma ($p<0.01$) and dairy flavor ($p<0.01$) than its control. Additionally, the freeze concentrate product was found to be significantly less sour ($p<0.02$) and exhibited a "more balanced" flavor profile than its control. Since the control was thicker, however, it was judged to have a slightly better mouth feel.

EXAMPLE 6

| Cream Cheese Standard Formulation Control | |
|---|---|
| Ingredient | Percent |
| Skim milk, liquid | 78.5–80.0 |
| Heavy Cream (37% fat) | 16.0 |
| Skim milk powder | 3.5–5.0 |
| Lactic acid culture (DSG 2000 Chr. Hansen's Laboratory) | 0.5 |

The standard control formulation was evaluated at two levels of skim milk powder, i.e. at 3.5% and 5 %. In each control, the skim milk liquid was replaced with reconstituted equal solids content freeze concentrate of Example 1 and the skim milk powder was replaced with the powder of Example 1, and designated tests 1 and 2. The results are shown below in connection with tests done at 36 hours and 7 days for the 3.5% skim milk powder and 7 days for the 5% skim milk powder.

| Evaluation at 36 Hours | | |
|---|---|---|
| Attributes | Control (3.5% Skim Powder) | Test-1 (3.5% FC Skim Powder) |
| 1. Color (0 = too light; 4 = about right; 8 = too dark) | 4.1 | 3.9 |
| 2. Dairy Aroma* | 2.3 | 3.3 |
| 3. Overall Flavor* | 6.4 | 6.5 |
| 4. Sweet* | 0.9 | 1.2 |
| 5. Salty* | 4.3 | 2.4 |
| 6. Sour* | 3.8 | 3.8 |
| 7. Bitter* | 0.0 | 0.0 |
| 8. Dairy* | 3.7 | 5.4 |
| 9. Off Flavor* | 1.2** | 0.0 |
| 10. Creaminess* | 6.2 | 6.9 |
| 11. Spreadability (0 = too thin, poor spread; 4 = about right; B = too thick, heavy, poor spread) | 2.1 | 2.9 |
| 11. Mouth feel (0 = very thin, watery; 4 = about right; 8 = too thick, heavy gummy) | 2.8 | 3.7 |
| 12. Mouth clearing (0 = too rapid; 4 = about right; 8 = slow) | 2.8 | 3.6 |
| pH | 4.3 | 4.5 |

0 = none; 8 = extensive
**Astringent

| Evaluation at 7 Days | | |
|---|---|---|
| Attributes | Control (3.5% Skim Powder) | Test-1 (3.5% FC Skim Powder) |
| 1. Color (0 = too light 4 = about right; 8 = too dark) | 4.0 | 4.0 |
| 2. Dairy Aroma* | 2.6 | 4.5 |
| 3. Overall Flavor* | 5.4 | 6.4 |
| 4. Sweet* | 0.4 | 1.0 |
| 5. Salty* | 1.4 | 1.4 |
| 6. Sour* | 4.0 | 3.1 |
| 7. Bitter* | 0.1 | 0.1 |
| 8. Dairy* | 4.1 | 5.0 |
| 9. Off Flavor* | 1.0 | 0.3 |
| 10. Creaminess* | 4.3 | 6.1 |
| 11. Spreadability (0 = too thin, poor | 5.5 | 4.3 |

| | Evaluation at 7 Days | |
|---|---|---|
| Attributes | Control (3.5% Skim Powder) | Test-1 (3.5% FC Skim Powder) |
| spread; 4 = about right; 8 = too thick, heavy, poor spread) | | |
| 11. Mouth feel (0 = very thin, watery; 4 = about right; 8 = too thick, heavy gummy) | 5.5 | 3.9 |
| 12. Mouth clearing (0 = too rapid; 4 = about right; 8 = slow) | 4.8 | 3.9 |
| pH | 4.5 | 4.5 |

0 = none; 8 = extensive

| | Evaluation at 7 Days | |
|---|---|---|
| Attributes | Control (5% Skim Powder) | Test-1 (5% FC Skim Powder) |
| 1. Color (0 = too light; 4 = about right; 8 = too dark) | 3.6 | 4.0 |
| 2. Dairy Aroma* | 2.1 | 3.8 |
| 3. Overall Flavor* | 6.6 | 6.3 |
| 4. Sweet* | 0.5 | 0.6 |
| 5. Salty* | 1.6 | 1.4 |
| 6. Sour* | 4.0 | 4.0 |
| 7. Bitter* | 0.1 | 0.1 |
| 8. Dairy* | 2.4 | 3.9 |
| 9. Off Flavor* | 0.3 | 0.0 |
| 10. Creaminess* | 3.0 | 4.8 |
| 11. Spreadability (0 = too thin, poor spread; 4 = about right; 8 = too thick, heavy, poor spread) | 2.1 | 3.3 |
| 11. Mouth feel (0 = very thin, watery; 4 = about right; 8 = too thick, heavy gummy) | 2.6 | 3.1 |
| 12. Mouth clearing (0 = too rapid; 4 = about right; 8 = slow) | 2.5 | 3.1 |
| pH | 4.5 | 4.5 |

0 = none; 8 = extensive

At 36 hours, the cream cheese produced with freeze concentrate ingredients were judged superior to the control in dairy aroma (p<0.04) and dairy flavor (p<0.01). Additionally, this product was also perceived as having better flavor balance, partly because of the absence of off flavors, as compared to the control. Texture ratings were not reliable comparison indicators since the systems were not thick enough because of the lack of stabilizers.

After seven days the cream cheese produced with freeze concentrate ingredients (3.5% skim milk powder) was still judged to be superior in overall flavor (p<0.03), creaminess (p<0.01) and "balance". The 5.0% skim milk powder systems were not perceived to be as good as the 3.5% systems. However, the 5.0% freeze concentrate system was judged superior to the control in terms of dairy aroma (p<0.01) and creaminess (p<0.01).

EXAMPLE 7

| White Sauce Standard Formulation Control | |
|---|---|
| Ingredient | Percent |
| Skim milk | 90.45 |
| Butter | 5.22 |
| All-purpose flour | 3.66 |
| Salt | 0.67 |

The skim milk of the control was replaced by the freeze concentrate of Example 1 and was designated as Test-1. The results were as shown below.

| Attributes | Control | Test-1 |
|---|---|---|
| 1. Dairy Aroma* | 4.4 | 3.4 |
| 2. Overall Flavor* | 5.0 | 5.2 |
| 3. Sweet* | 0.9 | 0.8 |
| 4. Sour* | 0.2 | 0.2 |
| 5. Salty* | 2.3 | 1.9 |
| 6. Bitter* | 0.0 | 0.0 |
| 7. Dairy* | 4.0 | 5.0 |
| 8. Creaminess* | 4.9 | 5.7 |
| 9. Grittiness/Chalkiness* | 0.5 | 0.2 |
| 10. Mouth clearing (0 = too thin, rapid; 4 = about right; 8 = too thick, slow) | 4.0 | 3.8 |

*0 = none; 8 = extensive

The white sauce prepared with freeze concentrate ingredient was judged superior to the control, especially in dairy flavor (p<0.05). However, the control sauce was judged to have a superior dairy aroma (p=0.02).

EXAMPLE 8

| Milk Chocolate Standard Formulation Control | |
|---|---|
| Ingredient | Percent |
| Cocoa butter | 31.2 |
| Chocolate liquor | 14.0 |
| Whole milk powder | 13.3 |
| Skim milk powder | 8.8 |
| Sugar | 31.9 |
| Lecithin | 0.5 |
| Vanillin | 0.3 |

This formulation meets the standard of identity.

The whole milk powder and the skim milk powder were replaced by the freeze concentrate powders of Examples 1 and 2 and designated as Test-1.

| Attributes | Control | Test-1 |
|---|---|---|
| 1. Chocolate Aroma* | 4.9 | 5.9 |
| 2. Dairy Aroma* | 0.5 | 1.3 |
| 3. Overall Flavor* | 4.3 | 6.0 |
| 4. Sweet* | 4.0 | 4.3 |
| 5. Sour* | 0.0 | 0.0 |
| 6. Salty* | 0.0 | 0.3 |
| 7. Bitter* | 1.9 | 0.8 |
| 8. Chocolate Flavor* | 3.6 | 5.1 |
| 9. Dairy* | 4.3 | 2.8 |
| 10. Off Flavor* | 0.0 | 0.0 |
| 11. Creaminess* | 1.4 | 2.9 |
| 12. Degree of Hardness (0 = too soft; 4 = about right; 8 = too hard) | 6.0 | 5.1 |
| 13. Melt | 6.3 | 5.3 |

| Attributes | Control | Test-1 |
|---|---|---|
| (0 = rapid; 4-typical; 8 = slow) | | |

0 = none; 8 = extensive

The milk chocolate prepared with freeze concentrate ingredients was judged to be significantly better than milk chocolate prepared with standard ingredients. The Expert Panel judged the test product to be superior in chocolate aroma ($p<0.01$), overall flavor ($p<0.01$), chocolate flavor ($p<0.03$), and dairy flavor ($p<0.04$), when compared to the control. Additionally, the test milk chocolate was perceived to be creamier ($p<0.01$) than the control, and exhibited better melt-in-the-mouth ($p=0.03$) characteristics.

What is claimed is:

1. In a formulated food containing a dairy product and having a significant dairy flavor, the improvement wherein the dairy product is at least in part one physical form of freeze concentrated liquid dairy product selected from the group consisting of milk, cream, buttermilk, and milk solids in sufficient amount so as to improve at least the dairy flavor of a formulated food selected from the group consisting of ice cream, ice milk, soft serve ice milk, yogurt, sour cream, cream cheese, white sauce, cream-style soup, milk chocolate and dairy-style salad dressing and mixtures thereof.

2. The food of claim 1 wherein the freeze concentrated liquid dairy product is in a dry powder physical form.

3. The food of claim 1 wherein the freeze concentrated liquid dairy product is in a reconstituted physical form.

4. The food of claim 1 wherein the freeze concentrated liquid dairy product has at least 20% by weight of total solids.

5. The food of claim 4 wherein the freeze concentrated liquid dairy product has at least about 30% total solids.

6. The food of claim 5 wherein the total solids is at least about 35% and up to 50%.

7. The food of claim 4 wherein the viscosity of the freeze concentrated liquid dairy product is between about 100 and 2,000 CST.

8. The food of claim 6 wherein the viscosity is between about 150 and 2,000 CST.

9. The food of claim 4 wherein the freeze concentrated liquid dairy product has between about 35% and 45% total solids and the viscosity thereof is between about 150 and 1,500 CST.

10. The food of claim 1 wherein the freeze concentrated liquid dairy product is freeze concentrated skim milk, reduced fat milk, whole milk, and mixtures thereof.

11. The food of claim 5 wherein the freeze concentrated liquid dairy product is skim milk.

12. The food of claim 5 wherein the freeze concentrated liquid dairy product is in the physical form of a dried mixture of freeze concentrated skim milk and cream.

13. The food of claim 1 wherein the frozen food is ice cream or soft serve ice milk.

14. The food of claim 1 wherein the freeze concentrated liquid dairy product has a lactose content less than that of a liquid dairy product from which the freeze concentrated liquid dairy product is made.

* * * * *